United States Patent
Citterio et al.

(10) Patent No.: US 9,238,615 B2
(45) Date of Patent: Jan. 19, 2016

(54) PROCESS FOR THE IODINATION OF AROMATIC COMPOUNDS

(75) Inventors: Attilio Citterio, Milan (IT); Luciano Lattuada, Bussero (IT); Gabriella Leonardi, Milan (IT); Fulvio Uggeri, Codogno (IT); Evelin Vignale, Isola d'Asti (IT); Massimo Visigalli, Settala (IT); Aurelia Ferrigato, Trecate (IT); Gabriele Meli, Gonessa (IT); Roberta Fretta, Collegno (IT); Roberta Mazzon, Volpiano (IT)

(73) Assignee: BRACCO IMAGING S.P.A., Milan (IT)

( * ) Notice: Subject to any disclaimer, the term of this patent is extended or adjusted under 35 U.S.C. 154(b) by 1052 days.

(21) Appl. No.: 13/265,165

(22) PCT Filed: Apr. 8, 2010

(86) PCT No.: PCT/EP2010/054624
§ 371 (c)(1),
(2), (4) Date: Oct. 19, 2011

(87) PCT Pub. No.: WO2010/121904
PCT Pub. Date: Oct. 28, 2010

(65) Prior Publication Data
US 2012/0041224 A1    Feb. 16, 2012

(30) Foreign Application Priority Data
Apr. 21, 2009  (EP) ................................. 09158319

(51) Int. Cl.
*C07C 227/16*    (2006.01)
(52) U.S. Cl.
CPC .................................. *C07C 227/16* (2013.01)
(58) Field of Classification Search
CPC .................................................. C07C 227/16
See application file for complete search history.

(56) References Cited

U.S. PATENT DOCUMENTS

| | | | | |
|---|---|---|---|---|
| 2,820,814 A * | 1/1958 | Ginsberg | ........................ | 560/47 |
| 4,001,323 A | 1/1977 | Felder et al. | | |
| 4,352,788 A * | 10/1982 | Felder et al. | ............... | 424/9.454 |
| 5,013,865 A | 5/1991 | Cross et al. | | |
| 5,075,502 A | 12/1991 | Kneller et al. | | |
| 5,362,905 A | 11/1994 | Villa et al. | | |
| 5,616,795 A | 4/1997 | Mauro et al. | | |
| 5,616,798 A | 4/1997 | Dugast-Zrihen et al. | | |
| 6,458,967 B1 * | 10/2002 | Detty et al. | ...................... | 549/13 |
| 2007/0219396 A1 | 9/2007 | Yamada et al. | | |

FOREIGN PATENT DOCUMENTS

| | | |
|---|---|---|
| CN | 1154689 A | 7/1997 |
| DE | 2547789 A1 | 6/1976 |
| EP | 0026281 A1 | 4/1981 |
| EP | 0773924 A1 | 5/1997 |
| GB | 1234558 A | 6/1971 |
| JP | 1976-082236 A | 7/1976 |
| JP | 1993-502230 A | 4/1993 |
| JP | 1994-345705 A | 12/1994 |
| JP | 1998-508874 A | 9/1998 |
| JP | 1998-330336 A | 12/1998 |
| JP | 10316639 A2 | 12/1998 |
| JP | 2001-526677 A | 12/2001 |
| JP | 2008-074722 A | 4/2008 |
| NL | 6918353 A | 6/1970 |
| RU | 2098131 C1 | 10/1997 |
| WO | 88-09328 A1 | 12/1988 |
| WO | 91/13636 A1 | 9/1991 |
| WO | 92-14695 A1 | 9/1992 |
| WO | 94-14478 A1 | 7/1994 |
| WO | 96/37459 A1 | 11/1996 |
| WO | 96-37460 A1 | 11/1996 |
| WO | 96-37461 A1 | 11/1996 |

(Continued)

OTHER PUBLICATIONS

Sugita et al. Chem Lett 1982, pp. 1481-1484.*
Butler, A. R. J. Chem. Ed. 1971, 36, p. 508.*
Patil et al. Tetrahedron Lett. 2005, 46, 7179-7181.*
Abe et al. Org. Lett. 2005, 7, 59-61 and its supporting information.*
Oshiro et al. J. Organomet. Chem. 1998, 569, pp. 195-202.*
Mattern, D. L. J. Org. Chem. 1984, 49, 3051-3053.*
Office Action for Japanese application No. 2012-506434, mail date Aug. 6, 2013 (English translation).

(Continued)

*Primary Examiner* — Matthew Coughlin
(74) *Attorney, Agent, or Firm* — Vivicar Law, PLLC

(57) ABSTRACT

The present invention relates to a process for the preparation of iodinated anilines; in particular, it relates to a process including the direct iodination, with suitably activated iodine, of 3,5-disubstituted anilines to the corresponding 3,5-disubstituted-2,4,6-triiodoanilines, which are useful intermediates for the synthesis of x-ray contrast media, and to the preparation of the contrast media themselves.

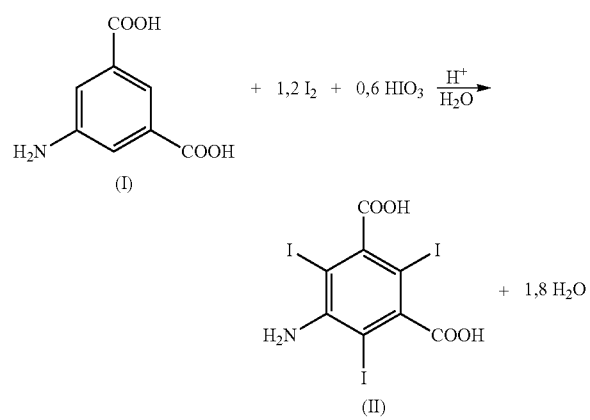

15 Claims, 8 Drawing Sheets

(56) References Cited

FOREIGN PATENT DOCUMENTS

| | | |
|---|---|---|
| WO | WO 9637458 A1 * | 11/1996 |
| WO | 97-05097 A1 | 2/1997 |
| WO | 97-47590 A2 | 12/1997 |
| WO | 98-24757 A1 | 6/1998 |
| WO | 98/52908 A1 | 11/1998 |
| WO | WO 0015266 A2 * | 3/2000 |
| WO | 00-32561 A1 | 6/2000 |
| WO | 03/013616 A1 | 2/2003 |
| WO | 2006/016510 A1 | 2/2006 |
| WO | 2009-103666 A2 | 8/2009 |

OTHER PUBLICATIONS

Kretzer, H., "Zur Kenntniss der Jodosobenzoesauren", Chem. Ber., No. 2, 1897, pp. 1943-1948, XP002530263.

Lutjens, Jacob, "Ueber das chemische Verhalten und die Oxydation der Tetrajodterephtalsaure, und fiber Trijoddiamidobenzoesaure", Chem. Ber., vol. 29, No. 3, 1896, pp. 2833-2839, XP002530263.

PCT International Search Report for PCT/EP2010/054624, mail date Jul. 7, 2010.

PCT Written Opinion of the International Searching Authority for PCT/EP2010/054624, mail date Jul. 7, 2010.

Decision for Grant of Patent for Russian application No. 2011147046, mail date Sep. 26, 2013 (English translation).

Office Action for Canadian application No. 2,759,342, mail date May 27, 2014.

Office Action for Mexican application No. MX/a/2011/010333, mail date Apr. 25, 2014 (English Translation).

Office Action for Chinese application No. 201080017568.4, mail date Jul. 1, 2013 (English translation).

Office Action for Russian application No. 2011147046, mail date Mar. 26, 2013 (English translation).

Hua, Wang, "Electrolysis of inactivated aromatic compounds—iodination study", Journal of Huiyang Normal University College, Dec. 31, 1988, No. 1, pp. 56-60 (English translation).

Office Action for Chinese application No. 201080017568.4, mail date Apr. 29, 2014 (English translation).

Office Action for Israeli application No. 215685, mail date Jun. 17, 2014 (with associate's Jul. 9, 2014 letter with translation of the Hebrew-language Office Action).

Baer, Erich et al., "Formation of Symmetric Azo-compounds from Primary Aromatic Amines by Lead Tetraacetate", Journal American Chem. Society, 1956, vol. 78, No. 12, pp. 2857-2858.

Furuichi, Ryusaburo et al., "Radioactive Iodine Exchange and the Dushman Reaction", Bulletin of the Chemical Society of Japan, 1973, vol. 46, No. 7, pp. 2008-2010.

Furuichi, Ryusaburo et al., "Rate of the Dushman Reaction in Iodic Acid at Low Iodide Concentration. Complexity of Iodic Acid", Bulletin of the Chemical Society of Japan, 1975, vol. 48, No. 3, pp. 745-750.

Patil, Bhagwan R. et al., "Regioselective iodination of hydroxylated aromatic ketones", Arkivoc, 2006, ISSN 1424-6376, pp. 104-108.

Office Action for Canadian application No. 2,759,342, mail date Mar. 19, 2015.

\* cited by examiner

PROCESS FOR THE IODINATION OF AROMATIC COMPOUNDS

CROSS-REFERENCE TO RELATED APPLICATIONS

This application is the national stage application of corresponding international application number PCT/EP2010/054624 filed Apr. 8, 2010, which claims priority to and the benefit of European application no. 09158319.5, filed Apr. 21, 2009.

The present invention relates to a process for the preparation of poly-iodinated aromatic compounds. More particularly, it relates to a process including the direct iodination of 3,5-disubstituted anilines to the corresponding 3,5-disubstituted-2,4,6-triiodoanilines, which are useful intermediates for the synthesis of x-ray contrast media, and to the preparation of the contrast media themselves.

BACKGROUND

Iodinated contrast agents are well-known compounds widely used in x-ray imaging diagnostic techniques. Suitable examples of the said compounds include, for instance, diatrizoate, iothalamate, ioxithalamate, metrizoate, iohexol, iomeprol, iopamidol, iopentol, iopromide, ioversol, ioxilan, iodixanol, iosarcol, iogulamide, ioglunide, iogluamide, acetrizoate, iodamide, iocetamide and metrizamide, all having a monomeric structure, and ioxaglate, iotrolan, iotasul, iodipamide, iocarmate, iodoxamate, iotroxate, iotrolan, and the like, that, instead, are dimers. Additional examples of iodinated contrast agents are described, for instance, in WO 94/14478 (Bracco).

As a common feature, their chemical structure shares a triiodinated aromatic nucleus which provides the enhanced contrast effect.

The said compounds may be prepared by a variety of routes, that generally include the iodination of given aromatic substrates, for instance of suitable 3,5-disubstituted phenols, which undergo triiodination on the available 2, 4 and 6 positions, thus leading to the corresponding 3,5-disubstituted-2,4,6-triiodophenols. These latter, in turn, may be further converted and processed through the so-called Smile's rearrangement, to the expected final compounds.

For a general reference to the above synthetic route and Smile's rearrangement see, for instance, WO 88/09328, WO 97/05097 and WO 00/32561 (Bracco).

Alternatively, the aromatic iodination may be performed on suitable anilines, so as to provide the corresponding 2,4,6-triiodoaniline derivatives, to be further converted and processed to the final radiographic agent, for instance as disclosed in U.S. Pat. No. 5,075,502.

The iodination step may be performed utilizing different procedures.

In this regard, in industrial processes currently used for preparing the above radiographic contrast agents, the iodination of the aromatic ring is generally carried out by using solutions of iodine mono-chloride (ICl) in concentrated hydrochloric acid (HCl) (44.5% I and 14% HCl) at high temperature (about 90° C.) or, alternatively, by means of analogous iodinating agents such as, for instance, $KICl_2$ or $NaICl_2$ in aqueous solution; see, for a general reference, WO 92/14695 (Guerbet), U.S. Pat. No. 5,013,865 (Mallinckrodt), WO 96/37458 and WO 96/37459 (Fructamine).

The above methods suffer from major drawbacks due to the extremely acidic working conditions, that become harder due to HCl produced during the reaction, and to the corrosive properties and the limited storage life of the iodinating agents.

In addition, relevant problems mainly arise from the presence of chlorine atoms within the iodinating agents themselves, (formed at the high reaction temperature needed for the exhaustive iodination of aniline substrates), that may lead to the formation of hardly removable chlorinated side-products, which may thus affect reaction yields and purity of the final compounds.

On the other side, and from a different point of view, it is an increasingly recognized need to have industrial manufacturing processes which can combine low production costs, high production efficiency and minimized environmental impact.

Thus, attempts have been devoted to address new iodination methods based on the use of iodinating agents alternative to iodine mono-chloride or derivatives thereof.

Among them are, for instance, the electrochemical iodination processes of 3,5-disubstituted anilines or of given 3,5-disubstituted phenols, as disclosed in WO 96/37461 and WO2009/103666, respectively.

Beside the above approaches, the alternative iodination of aromatic nuclei with iodine suitably activated with an oxidizing agent has also been experienced.

For instance, the iodination of given phenol derivatives, referred to as ortho-hydroxy substituted aromatic carbonyl compounds, in the presence of molecular iodine activated with a strong oxidizing agent, including iodic acid, has been described by Patil et al. in *Tetrahedron Letters* 2005, 46, 7179-7181, and in *ARKIVOC* 2006, 104-108.

This art is, however, silent on the possibility of exploiting that disclosed synthetic approach, namely the combined use of molecular iodine and an oxidizing agent, to iodinate or poly-iodinate aniline or aniline derivatives.

US 2007/0219396 discloses a method for producing 2-amino-5-iodobenzoic acid by iodination of 2-aminobenzoic acid, solubilized in acetic acid, with iodine and in the presence of an oxidizing agent, especially hydrogen peroxide.

This application, however, does not mention or suggest the possibility of exploiting the disclosed procedure to provide poly-iodinated compounds and, in particular, triiodinated aniline derivatives that, indeed, would hardly have been achieved under the disclosed iodination conditions, as evidenced by the Comparative Example 1 of the following experimental section.

The use of iodine and iodic acid to produce 3-amino-2,4,6-triiodobenzoic and 3,5-diamino-2,4,6-triiodobenzoic acids is also mentioned in *Chem. Ber.*, 1897, 30 (2), 1943-1948 and in *Chem. Ber.*, 1896, 29 (3), 2833-2839, respectively.

These references, however, are quite deficient in the full description of the iodinating conditions used, so as to prevent their accurate reproduction.

In any case, the disclosed iodinating conditions and the amount of iodinating agent, in particular of iodic acid, seems far to be sufficient to allow triiodination of the substrate, at least with appreciable yield and purity, as discussed in greater detail in the Comparative Example 2 of the experimental section below.

Moreover, in both of the cited articles, the obtained brown precipitate needs to be washed with sulfuric acid, solubilized in diluted ammonia and then precipitated with sulfuric acid to have a product of the desired purity.

In this respect, it is worth noting that the use of strong oxidizing conditions with aniline or even halogenated anilines is known to lead to the formation of mixtures of colored by-products, mainly azo-compounds deriving from oxidative coupling reactions involving the aromatic amino group (see, for instance, Erich Baer and Anthony L. Tosoni, *J. Am. Chem. Soc.*, 1956, 78 (12), 2857-2858), while all the above art does neither address nor even suggest how to solve this problem.

For contrast, the need of collecting process intermediates and final compounds with a high degree of purity is of utmost importance in order to optimize, to a significant extent, the purification steps required for the final agent, that has to be in compliance with the strict purity profile and limits imposed by the Pharmacopoeia, in particular for products intended for the administration.

For instance, the analytical specifications fixed by the EP Pharmacopoeia for the 5-amino-2,4,6-triiodoisophthalic acid, are:
Loss on drying ≤3.5%
Title: 98.0-102%
Ashes: ≤1.0%
Total related substances: ≤1% (intended as the sum of all known and unknown impurities, mainly represented by partially iodinated compounds and chlorinated compounds) of which the sum of the chlorinated impurities must be ≤0.35%.

We have now found that the triiodination of suitable 3,5-disubstituted anilines can be advantageously carried out in high yields and purity by using a iodinating system comprising molecular iodine and an oxidizing agent overcoming the above major drawbacks.

OBJECT OF THE INVENTION

The present invention provides a process for the triiodination of 3,5-disubstituted anilines with suitably activated iodine and, also, a method for the preparation of x-ray contrast agents including the above iodination step.

More particularly, a first object of the present invention is represented by a process for the preparation of 5-amino-2,4,6-triiodoisophthalic acid of formula

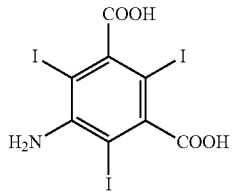

(II)

which process comprises iodinating 5-aminoisophthalic acid of formula (I) or a salt thereof

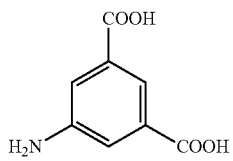

(I)

with molecular iodine in the presence of a suitable oxidizing agent.

The process of the invention is particularly advantageous as it enables the complete triiodination of the 5-aminoisophthalic acid of formula (I), or of the corresponding salt thereof, and leads to the corresponding 5-amino-2,4,6-triiodoisophthalic acid of formula (II) in high yields and purity.

Remarkably, and unlike previous teachings on oxidability of anilines, the above process is not affected by the presence of side-products deriving from the partial iodination of the aromatic ring or from the oxidative coupling occurring on the amino group.

Advantageously, therefore, the process of the invention does not require any step of purification of the obtained triiodinated compound that is isolated from the crude solution by filtration and, fulfilling the analytical specifications for the industrially produced intermediate, can, thus, be used as such in the next reaction step to the iodinated agent of interest.

In addition, by efficiently consuming all of the added molecular iodine and by producing water as the sole reaction by-product, as per details below, the need of subsequent steps for recovering and recycling unreacted iodine and to treat industrial flow streams may be minimized to a very significant extent.

As formerly reported, in the process of the instant invention, the iodination reaction leading to the formation of the 5-amino-2,4,6-triiodoisophthalic acid of formula (II) occurs with molecular iodine ($I_2$) in the presence of a suitable oxidizing agent, according to the well-known electrophilic substitution mechanism.

To this extent, the effective iodinating specie may be represented by iodine cations ($I^+$), at least a portion of which is first generated by molecular iodine ($I_2$), while the unreactive iodide counter-ions ($I^-$) thus produced are conveniently oxidized by the oxidizing agent back to molecular iodine, or even to iodine cations with a higher oxidation state, thus making them still available for the iodination of the aromatic ring.

From the foregoing, and unless otherwise provided, suitable oxidizing agents for use in the process of the invention are those commonly employed on industrial scale and that are capable of oxidizing iodide ions to a higher oxidation state active for iodination, as detailed in the following paragraphs.

Suitable examples of oxidizing agents thus include, for instance, nitric acid, sulfuric acid, iodic acid, sulfur trioxide, hydrogen peroxide, ozone, and the like.

Generally speaking, the choice of the oxidizing agents will depend from several factors among which is, for instance, the operating conditions enabling them to properly exert their oxidative function during the course of the reaction, so as to bring to the formation of the desired compound, as well as their availability.

As such, and according to a first embodiment of the process of the invention, the oxidizing agent is preferably selected between hydrogen peroxide and iodic acid, the latter being even more preferred.

When molecular iodine is used in the presence of iodic acid ($HIO_3$), in fact, the unreactive iodide ions formed in the iodination reaction are converted back to molecular iodine through the so-called Dushman reaction, according to the following reaction Scheme 1

$$IO_3^- + 5I^- + 6H^+ \rightarrow 3I_2 + 3H_2O$$

Remarkably, this reaction further leads to a convenient reduction of the iodate ions ($IO_3^-$) to molecular iodine, still available for the iodination of the aromatic ring (see, for instance, Furuichi, R. and Liebhafsky, H. A. Radioactive iodine exchange and the Dushman reaction. *Bull. Chem. Soc. Japan* 1973, 46, 2008-2010 and *Bull. Chem. Soc. Japan* 1975, 48, 745-750).

As a result, a complete triiodination of the 5-aminoisophthalic substrate is achieved so as to obtain, very advantageously, the desired compound of formula (II) in high yields and purity, by consuming a stoichiometric amount of iodinating species, that is calculated as the sum of both of the added $I_2$ and $HIO_3$, as per the following general reaction Scheme 2.

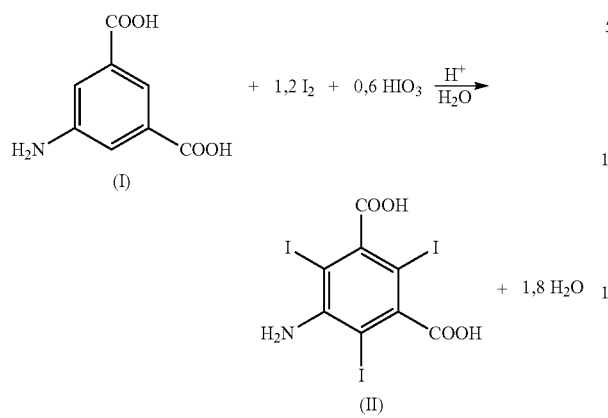

In other words, the combined use of iodine and iodic acid, as per the preferred embodiment of the invention, enables the complete triiodination of the aromatic substrate of formula (I) by avoiding, on one side, the need of any excess of iodinating agent, especially of molecular iodine and, on the other, the formation of by-products, especially unreactive poly-iodide ions, for instance of $I_3^-$ ions, mainly deriving from the combination of $I_2$ with iodide ions.

In this respect, it is clear to the skilled person that the equivalent ratio between the 5-aminoisophthalic acid substrate and the iodinating specie considered, as said, as the sum of both $I_2$ and $HIO_3$, has to be at least equal to 1:3, as per the former general Scheme 2.

Kept safe this point, in the process of the instant invention the triiodination of the 5-aminoisophthalic substrate with iodine and iodic acid will be carried out by using at least one mol of molecular iodine for each mol of 5-aminoisophthalic substrate of formula (I). Preferably, the molar ratio between iodine and 5-aminoisophthalic substrate (I) [$I_2$/(I)] will vary from 1 to 1.5, more preferably from 1 to 1.3; even more preferably, the triiodination of the 5-aminoisophthalic substrate with iodine and iodic acid will be carried out by using only 1.2 mol of iodine per mol of substrate (I).

On the other side, because of the stoichiometry of the involved reaction, the molar ratio between iodine and iodic acid shall be at least equal to 1:0.5, while the molar ratio between 5-aminoisophthalic substrate (I) and iodic acid shall be at least equal to 1:0.6.

Accordingly, in a particularly preferred embodiment of the invention, the triiodination of the 5-aminoisophthalic substrate with iodine and iodic acid will be carried out by using a molar ratio 5-aminoisophthalic substrate (I):iodine:iodic acid of 1:1.2:0.6.

However, a slight excess, over the minimum stoichiometric amount, of iodic acid over molecular iodine may, optionally, be used with equally good results, as reported in the experimental section.

Accordingly, in one different embodiment of the invention, a molar ratio iodine to iodic acid ranging from 1:0.5 to about 1:1 and, more preferably, from 1:0.5 to about 1:0.8, will be employed.

In this respect, a minimum amount of sodium bisulfite may, for instance, be added to the final reaction medium in order to destroy any optional residual iodinating species. In this case, the optimal quantity can, for instance, be potentiometrically determined as the minimum amount of bisulfite leading to a redox potential of the final mixture preferably lower than 250 mV.

The iodination reaction of the invention, comprising using the iodinating system $I_2/HIO_3$, as set forth above, is preferably carried out in the presence of a polar solvent, and preferably a protic one, and under acidic conditions.

Non limiting examples of suitable solvents may thus include, for instance: water or aqueous solvents, including aqueous saline solutions, lower alcohols $C_1$-$C_4$, for instance methanol or ethanol, and hydroalcoholic mixtures thereof, dioxane, glycols such as, for instance, diethylene glycol, triethylene glycol, and polyethylene glycols like PEG 600, PEG 1000 or PEG 2000 or mixtures thereof, and aqueous mixtures thereof.

Preferred solvent are water or aqueous solutions, methanol, ethanol and dioxane as well as mixture thereof with water or an aqueous solution.

In a particularly preferred embodiment of the invention, the iodination process is carried out in water or aqueous solvents, that significantly contributes to reduce the costs and the environmental impact of the provided process.

In an even most preferred embodiment, the iodination process is carried out directly on the crude aqueous solution deriving from the industrial process for the preparation of the starting 5-aminoisophthalic substrate, for instance carried out as disclosed in WO 96/37459, optionally diluted with water and suitably acidified.

Proper acidic conditions are achieved in the presence of a suitable acid including, for instance, phosphoric, metanesulfonic or sulfuric acid, e.g. 96% $H_2SO_4$. Preferably, suitable acidic conditions are obtained by using 96% $H_2SO_4$, for instance in an amount ranging from about 0.5 to 2 mol and, preferably, from 0.7 to 1.5 mol of $H_2SO_4$ per mol of substrate compound (I).

To this extent, and according to a preferred embodiment of the invention, the iodination reaction is carried out at pH (of the reaction mixture) lower than 3.5, preferably comprised from 1 to 3.0 and, even more preferably, from 1.5 to 2.5, preferably achieved by using concentrated $H_2SO_4$.

In this respect, it is worth noting that once acidified at this latter range with sulfuric acid, the pH of the reaction is advantageously self-maintaining from 1.5 to 2.5 through the reaction time, while the addition of a base, for instance diluted NaOH, is necessary to keep the reaction pH around 3.

Interestingly, despite the fact that the above pH conditions are known to strongly deactivate any electrophilic substitution on aniline substrates, these conditions, apparently unfavorable, allow to obtain 5-amino-2,4,6-triiodoisophthalic acid with very high yields, and, moreover, essentially uncontaminated by partial iodination side-products or colored impurities.

Instead, at higher pH, for instance higher than 4, the desired triiodinated product may be obtained, but with lower yields and purity, so as to require further purification to achieve the analytical specifications fixed for the industrially produced intermediate.

When operating under such acidic conditions, the aromatic substrate undergoing triiodination is represented by the 5-aminoisophthalic acid of formula (I), either employed as starting material of the process or, alternatively, formed in situ from the corresponding salt.

This latter, unless otherwise provided in the present description, is preferably selected from alkali or alkali-earth metal salts of 5-aminoisophthalic acid such as, for instance, sodium, lithium, potassium, calcium or magnesium salts.

Particularly preferred, among them, is the 5-aminoisophthalic acid sodium salt, which can be used as such, i.e. as a pure compound or, alternatively, as comprised within a crude solution directly deriving from a previous step in the process for the preparation of triiodinated contrast agents, for instance iopamidol.

Interestingly, according to the above operating conditions, i.e. in the presence of an acidic aqueous environment, 5-amino-2,4,6-triiodoisophthalic acid is unexpectedly obtained in high yields and purity despite of the practical insolubility of the starting aromatic substrate to be iodinated.

When 5-aminoisophthalic acid is used as starting material, in fact, a proper amount of this substrate compound is first suspended and thus maintained in the reaction medium before iodination reaction takes place. Alternatively, when an aqueous solution of the corresponding salt is used, for instance by starting from the industrial aqueous solution of the corresponding sodium salt, the acidic environment is such to promote the precipitation of the insoluble acid of formula (I) that is kept in suspension according to conventional means, e.g. under magnetic or mechanical stirring.

The same goes for the iodine, which is loaded as solid in the suspension of the isophthalic substrate, properly acidified as said.

To this extent, the proper amount of iodic acid may be then added to the obtained suspension at once or, alternatively, gradually, either continuously over time or portion-wise according to conventional means, thus causing the progressive partial solubilization of the 5-aminoisophthalic substrate that is thus progressively converted to the desired triiodinated product.

More particularly, and according to the following experimental section, iodic acid may be quickly added, for instance in a few minutes or even at once, to a reaction suspension more mildly acidified, for instance to pH≥2.5, i.e. around 3. Instead, when operating under stronger acidic conditions, i.e. at a pH about 2 or even lower, a slow additions of iodic acid is preferred, that may be effected over time, for instance in a time of up to 6 hours, and preferably, in a time from 2 to 6 hours.

In this respect, an aqueous solution of the oxidizing agent can profitably be used, with a concentration ranging, for instance, from 8 to 50% (w/w).

The iodination reaction is carried out in a temperature ranging from 50° C. to 85° C.

For instance, in one option, the reaction temperature during the process can be kept constant to a value comprised from about 60° C. to 85° C. and, preferably, from about 65° C. to 80° C., by operating according to conventional methods. Alternatively, all reactants can be loaded at room temperature thus giving a mixture that is then heated to a temperature ranging from 65 to 80° C., or, again, the iodinating agents ($I_2$ and $HIO_3$) can be added to a suspension heated to about 45° C. and, then, to raise and keep the reaction temperature from 65° C. and 80° C., as per the following experimental section.

The reaction time may vary according to the selected operative conditions and, generally, may range from about 2 to about 10 hours, more preferably from 5 to 8 hours.

Typically, by working at the formerly given temperatures, the process may reach the solvent boiling point, particularly when lower boiling solvents, like methanol, are employed. In addition, the partial sublimation of the iodine might also occur, even if the sublimed amount remains negligible when the reaction temperature is kept within the former range of values.

Nevertheless, standard cooling or condensing equipments may, for instance, be used to condensate both the solvent and the sublimate iodine that is then recycled to the reaction mixture according to conventional methods, for instance by adding small amounts of fresh solvent.

In this respect, it is worth noting that while the use, taught by the cited art (US 2007/0219396), of the acetic acid as a reaction solvent solves the problem of the iodine solubilization, it does not, conversely, contribute to increase the solubilization of the 5-aminoisophthalic acid, which remains insoluble in acetic acid even heated to 80° C. Moreover, disadvantageously, it does not allow the simple recovery of the iodination product, namely the 5-amino-2,4,6-triiodoisophthalic acid, that does not precipitate quantitatively from acetic acid, not even cooled to room temperature, unless properly diluted with water.

Still in addition, the solubility of the $HIO_3$ in acetic acid is very low. Therefore, when this oxidizing agent is added to an acetic reaction medium not properly diluted with water, as per the conditions taught by the cited art, it leads to the formation of a non-homogeneous phase that significantly reduces its efficiency in activating the iodine, as evidenced by the provided Comparative Example 1, of the following experimental section.

The above drawbacks may not be solved working under the iodinating conditions of the Chem. Ber. articles, that, indeed, teach using an acidic aqueous medium as diluted as to allow, on one hand, the desired solubilization of the starting substrate, but, on the other hand, most probably contribute to prevent the precipitation of the triiodinated compound of the invention, namely the 5-amino-2,4,6-triiodoisophthalic acid, that does not precipitate from the crude solution even cooled to room temperature, as evidenced by the provided Comparative Example 2 of the following experimental section.

In addition, the cited *Cher. Ber.*, 1897, 30 (2), 1943-1948 article teaches the use of a iodinating solution prepared a part by solubilization of solid $I_2$ in aqueous KOH (or NaOH), followed by addition of solid $HIO_3$ and subsequent dilution with water.

To this extent, beyond that the cited article does not refer neither the volume of KOH aqueous solution used nor its concentration, it is worth noting that the suggested amount of $HIO_3$ used to prepare the said iodinating mixture is insufficient to convert-back all the iodide ions formed in the iodination reaction. This necessarily implies, on one hand, the need of using an excess of iodine over the minimum stoichiometric amount required, for contrast, by the iodination process of the instant invention. On the other hand, it further results in the unwanted accumulation of iodide ions in the reaction medium, that may likely affect the purity of the iodination product and its consistency with analytical specifications for the industrially produced intermediate.

It is clear to a skilled person that alternative iodinating systems among those formerly reported and comprising molecular iodine in the presence of an oxidizing agent other than iodic acid, for instance hydrogen peroxide, and operative conditions thereof, are also to be regarded as comprised within the scope of the invention.

From all the foregoing it should be clear to a skilled practitioner that the process of the instant invention, essentially, comprises: obtaining a suspension of 5-aminoisophthalic acid into an aqueous solvent properly acidified, namely having a pH lower than 3.5, and adding solid $I_2$ and $HIO_3$ to the said suspension.

In greater details and according to a practical preferred embodiment of the invention, a proper amount of the 5-aminoisophthalic substrate is suspended or solubilized, as the case may be, into an aqueous solvent, typically water. The obtained solution/suspension is firstly diluted to a substrate concentration ranging from 8% to 3% (w/w) and, preferably, from 5% to 3%, and then acidified at pH lower than 3.5, preferably around 2, with a suitable amount of acid, for instance with 96% $H_2SO_4$.

Preferably, a crude solution directly obtained from the industrial process and comprising the 5-aminoisophthalic substrate as sodium (mainly monosodium, though disodium is not excluded) salt, at a concentration typically ranging around 7-8% (w/w), is used as starting material. This crude solution is then diluted, typically with water, to the above concentration range and then acidified at the aforementioned values, for instance with 96% $H_2SO_4$. Solid $I_2$ is then added to the obtained suspension of the 5-aminoisophthalic acid that is kept under stirring and heated at the temperature values formerly indicated.

A proper amount of an aqueous solution of $HIO_3$ is slowly added into the suspension, thus causing the progressive conversion of the 5-aminoisophthalic substrate into the desired triiodinated product.

By proceeding with the addition of $HIO_3$ up to completion, the formed 5-amino-2,4,6-triiodoisophthalic acid precipitates from the reaction mixture as a solid. At this point, the acidification of the crude reaction, for instance with 96% $H_2SO_4$, at a pH around 1 and cooling of the mixture to room temperature favors the almost complete precipitation of the triiodinated compound. Moreover, the addition of a minimum amount of sodium bisulfite (to the final crude mixture) allows to definitely destroy any optional residual iodinating agent and to obtain an even purer solid product that is filtered and dried.

The filtered compound is pure and ready to be used in the next steps for the preparation of the desired contrast agent without the need of any further purification.

On the other side, once obtained, the 5-amino-2,4,6-triiodoisophthalic acid of formula (II) may be then easily converted into the desired X-ray contrast agent by working according to known methods.

In this respect, the process object of the present invention is of general applicability and provides, very advantageously, a route for the preparation of iodinated contrast agents starting from the intermediate 5-amino-2,4,6-triiodoisophthalic acid.

Hence, it is a further object of the present invention a process for the preparation of the compounds of formula (III) below

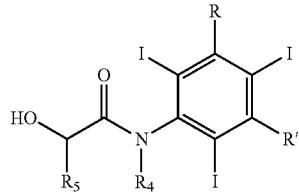

wherein:
R and R' represent, the same or different from each other, a group selected from carboxy (—COOH), carboxyester (—COOR$^1$) and carboxamido (—CONH$_2$, —CONHR$^1$ or —CONR$^2$R$^3$), wherein R$^1$, R$^2$ and R$^3$ are, the same or different from each other, a straight or branched $C_1$-$C_4$ alkyl group optionally substituted by one or more hydroxyl groups, and R$^4$ and R$^5$ are, the same or different from each other, hydrogen or a straight or branched $C_1$-$C_6$ alkyl group optionally substituted by one or more hydroxyl or $C_1$-$C_6$ alkoxy groups, the said process comprising the preparation of an intermediate compound of formula (II) through the process of the instant invention.

More preferably, the said process comprises:
a) preparing 5-amino-2,4,6-triiodoisophthalic acid of formula (II)

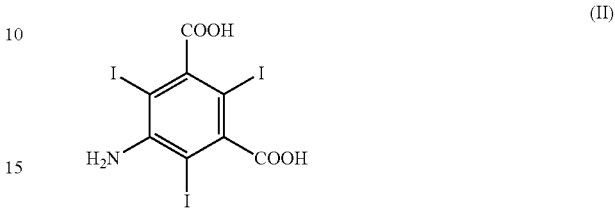

by iodinating 5-aminoisophthalic acid of formula (I) or a salt thereof

with molecular iodine in the presence of a suitable oxidizing agent;
b) converting the compound of formula (II) in the corresponding acid dichloride, and
c) using the dichloride as an intermediate compound for the preparation of the desired compounds of formula (III).

According to the said process, the iodination step a) is carried out as extensively reported in the previous sections whilst subsequent steps, comprehensive of experimental operative conditions and optional variants thereof are all to be performed according to conventional methods reported in the art and including, essentially, the conversion of 5-amino-2,4,6-triiodoisophthalic acid (II) into the corresponding acid dichloride according to known methods, for instance in the presence of thionyl chloride; its subsequent condensation with 2-[(acetyloxy)]propionic acid chloride, so as to give rise to the corresponding 5-carboxamido derivative and, finally, the condensation of this latter with serinol and subsequent work-up including any possible cleavage of protecting groups, so to obtain the expected final compound.

Preferably, the instant process may be applied to the preparation of a compound of formula (III) in which both R and R' are a —CONH—CH(CH$_2$OH)$_2$ group, R$^4$ is hydrogen and R$^5$ is a methyl group, commonly known as Iopamidol, or according to an equally preferred embodiment, for the preparation of a compound of formula (III) in which both R and R' are a —CONH—CH$_2$—CH(OH)CH$_2$OH, R$^4$ is methyl and R$^5$ is hydrogen, commonly known as Iomeprol.

Accordingly, an additional object of the instant invention relates to a process for the preparation of Iopamidol or Iomeprol that is characterized in that it comprises starting from a compound of formula (II) obtained through the process of the instant invention.

In the said process, as said the preparation of the starting compound of formula (II) is carried out as formerly widely reported, while subsequent steps, comprehensive of experimental operative conditions and optional variants thereof, are performed according to conventional methods and operative conditions for instance, disclosed in WO 96/037459, WO 96/037460, U.S. Pat. No. 5,362,905, WO 97/047590 and WO 98/24757, EP0026281.

Further details concerning the process of the invention are reported in the following experimental section, with the sole aim to better illustrate the present invention, without representing any limitation to it.

EXPERIMENTAL SECTION

Characterization of the Obtained Compound

Figure 1:
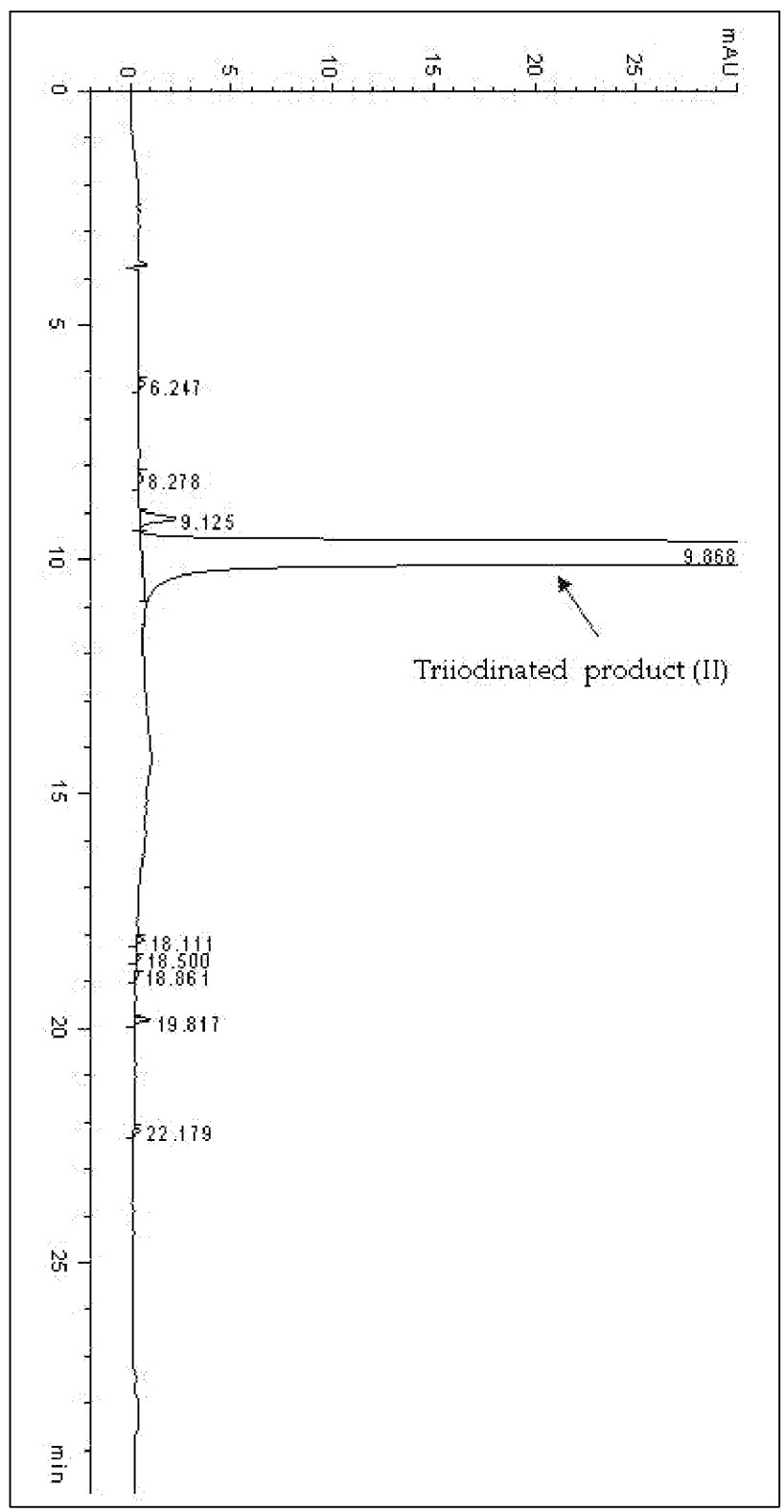
FIG. 1: HPLC analysis of the iodinated product of Example 3.
Figure 2:
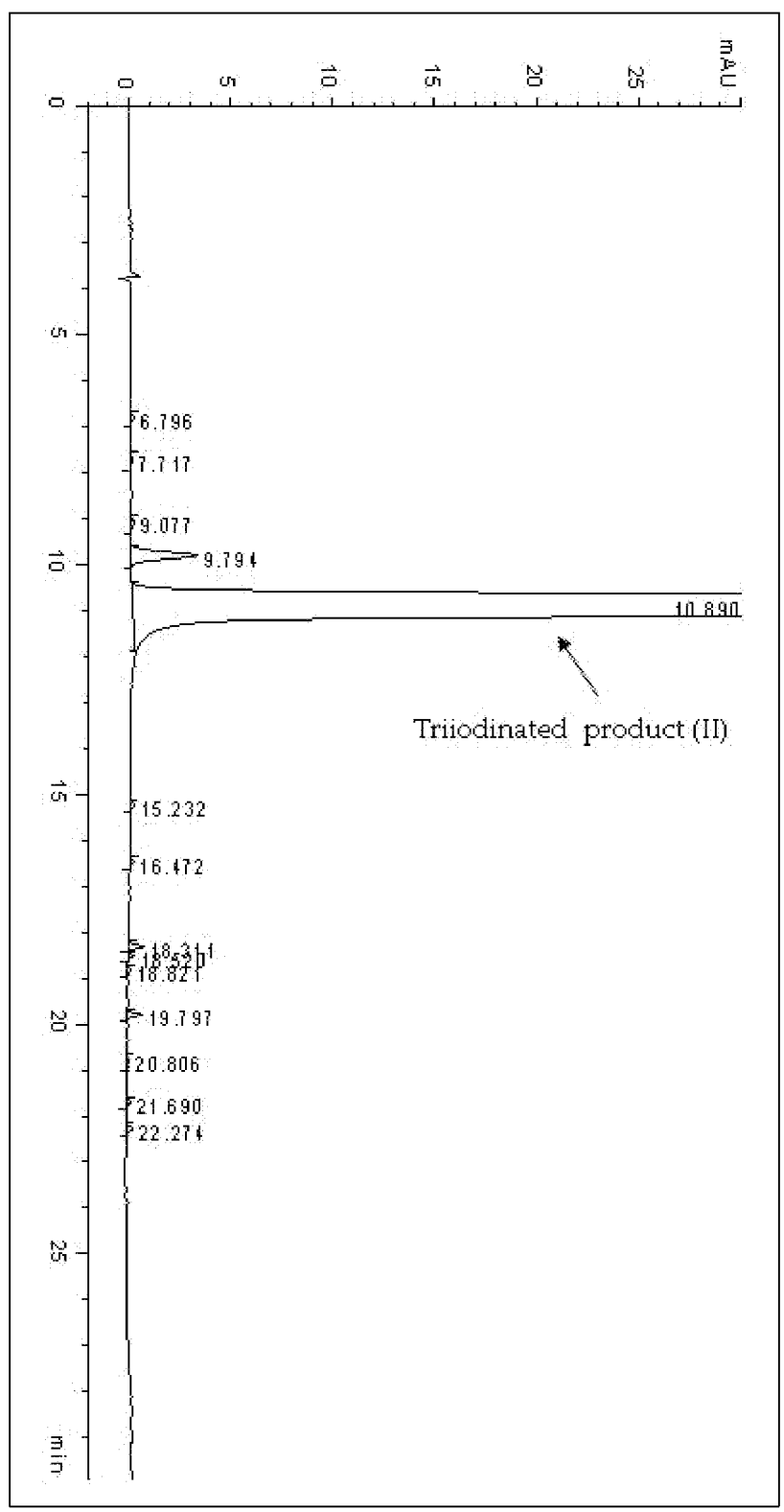
FIG. 2: HPLC analysis of the iodinated product of Example 4.

The purity of the obtained 5-amino-2,4,6-triiodoisophthalic acid has been determined by HPLC by comparison with a standard (pure compound) or by using benzoic acid as internal standard.
General Procedure
HPLC Chromatographic Method
Stationary phase: Zorbax SB-Phenyl 80 Å 5 μm, 250×4.6 mm (Agilent Technologies)
Mobile phase:
  A: 0.015 M $NaH_2PO_4$ + 0.028 M $H_3PO_4$
  B: $CH_3CN$
Elution:
  gradient elution
  gradient table:

| t (min) | phase A (%) | phase B (%) |
|---|---|---|
| 0 | 93 | 7 |
| 6 | 93 | 7 |
| 20 | 62 | 38 |
| 25 | 40 | 60 |

Temperature: 45° C.
Detection: UV (240 nm)
Flow: 1 mL/min
Sample concentration: 5 mg/mL
Injection: 10 μL Example 1

In a 250 mL three necked round bottom flask equipped with thermometer, condenser and magnetic stirrer, a solution of 5-aminoisophthalic acid (I) sodium salt in $H_2O$ corresponding to 3.86% (w/w) of acid (129.42 g of solution; 27.6 mmol) was loaded and acidified at pH around 1 with 96% $H_2SO_4$ (2 mL; 35.3 mmol). Then solid $I_2$ (8.42 g; 33.2 mmol) was added, the mixture was heated at 72° C. by means of an oil bath, and a 18.65% (w/v) solution of $HIO_3$ in $H_2O$ (20 mL; 21.2 mmol) was added to the heated mixture over 5.2 h through syringe pump. After additional 1 h at 72° C. (total reaction time 6.2 h) the reaction mixture was cooled at room temperature and filtered; the solid was washed with $H_2O$ and dried to give 5-amino-2,4,6-triiodoisophthalic acid (II) (12.74 g; 22.8 mmol) as a pale pink solid. Yield 82.6%. The product analyzed by HPLC, by comparison with a standard, fulfilled the analytical specifications for 5-amino-2,4,6-triiodoisophthalic acid industrially produced.

Example 2

In a 250 mL three necked round bottom flask equipped with thermometer, condenser and magnetic stirrer, a solution of 5-aminoisophthalic acid (I) sodium salt in $H_2O$ corresponding to 3.86% (w/w) of acid (129.42 g of solution; 27.6 mmol) was added and acidified at pH around 1 with 96% $H_2SO_4$ (2 mL; 35.3 mmol); then solid $I_2$ (5.26 g; 21.5 mmol) was added and the mixture was heated at 85° C. by means of an oil bath. A 3.08% (w/v) solution of $H_2O_2$ in $H_2O$ (25 mL; 22.6 mmol) was slowly added over 8.5 h through a syringe pump; at the end additional solid $I_2$ (5.26 g; 21.5 mmol) was added. Respectively after 0.5 h, 2.5 h and 6 h at 85° C. three portion of a 7% (w/v) solution of $H_2O_2$ in $H_2O$ (3×10 mL; total 61.7 mmol) was slowly added over 1.7 h each through a syringe pump. The reaction mixture is kept at 85° C. for additional 1 h then cooled at room temperature and filtered; the solid was washed with $H_2O$ and dried to give 5-amino-2,4,6-triiodoisophthalic acid (II) (12.41 g; 22.2 mmol) as pale brownish solid. Yield 80.4%. The product was analyzed by HPLC by comparison with a standard and fulfilled the analytical specifications for 5-amino-2,4,6-triiodoisophthalic acid industrially produced.

Example 3

In a 3 L jacketed reactor equipped with thermometer, condenser and mechanic stirrer, a solution of 5-aminoisophthalic acid (I) sodium salt in $H_2O$ corresponding to 6.7% (w/w) of acid (1194 g of solution; 0.442 mol) was loaded, diluted with $H_2O$ (636 mL) and acidified (to pH 2.8) with 50% $H_2SO_4$ (73.63 g; 0.375 mol). The mixture was then heated to 45-50° C. and added with solid $I_2$ (134.5 g; 0.530 mol). A 50% (w/v) solution of $HIO_3$ in $H_2O$ (93.22 g; 0.265 mol) was added in 15 min, the obtained mixture is heated to 75° C. and maintained at this temperature for 4 hours, during which the mixture pH is self-maintained in the range between 2.5 and 2.2. Additional 50% $H_2SO_4$ (430 g; 2.190 mol) was then added to the crude suspension in 1.5 h (to a pH<1) and the obtained suspension is cooled to room temperature in 2 h. A 18% (w/w) solution of sodium bisulfite (13.48 g; 0.023 mol) was added under stirring. The solid was then filtered, washed with $H_2O$ (200 mL) and dried to give 5-amino-2,4,6-triiodoisophthalic acid (II) (228.9 g; 0.409 mol) as pale pink solid. Yield 92.6%. The product was analyzed by HPLC by comparison with a standard and fulfilled the analytical specifications for 5-amino-2,4,6-triiodoisophthalic acid industrially produced.

Example 4

In a 1.5 L jacketed reactor equipped with thermometer, condenser and mechanic stirrer, a solution of 5-aminoisophthalic acid (I) sodium salt in $H_2O$ corresponding to 6.7% (w/w) of acid (597 g of solution; 0.221 mol) was loaded, diluted with H$_2$O (318 mL) and acidified with 50% H$_2$SO$_4$ (30.32 g; 0.155 mol). The mixture was heated to 45-50° C. and I$_2$ (67.26 g; 0.265 mol) was added. A 50% (w/w) solution of HIO$_3$ in H$_2$O (46.60 g; 0.132 mol) was added in 15 min (pH of the obtained mixture: about 3) and the mixture was heated to 75° C. for 4 h, (during which the pH of the mixture drops to about 2). 50% H$_2$SO$_4$ (222 g; 1.13 mol) was then added (to a pH<1) in 2 h and the suspension was cooled down to 25° C. in 2 h. A 18% (w/w) solution of sodium bisulfite (5.91 g; 0.010 mol) was added, the mixture was kept under stirring, then the solid was filtered, washed with H$_2$O (150 mL) and dried to give 5-amino-2,4,6-triiodoisophthalic acid (II) (109.8 g; 0.196 mol) as whitish solid. Yield 88.9%. The product was analyzed by HPLC by comparison with a standard and fulfilled the analytical specifications for 5-amino-2,4,6-triiodo-isophthalic acid industrially produced.

Example 5

In a 1 L jacketed reactor equipped with thermometer, condenser and mechanic stirrer, a solution of 5-aminoisophthalic acid (I) sodium salt in H$_2$O corresponding to 6.7% (w/w) of acid (373 g of solution; 0.138 mol), H$_2$O (200 mL), a 50% (w/w) solution of HIO$_3$ in H$_2$O (29.12 g; 0.083 mol), 50% H$_2$SO$_4$ (15.71 g; 0.080 mol) and I$_2$ (42.03 g; 0.166 mol) were loaded at room temperature. The mixture was heated to 60° C. in 30 min, acidified with 50% H$_2$SO$_4$ (7.64 g; 0.039 mol), and then heated to 75° C. for 3 h (pH 1.9). The resulting suspension was then further acidified (to a pH<1) with 50% H$_2$SO$_4$ (120 g; 0.612 mol), slowly added in 2 h, and cooled down to 25° C. in 2 h. A 18% (w/w) solution of sodium bisulfite was then added, under stirring, to the mixture up to a redox potential <250 mV. The solid was then filtered, washed with H$_2$O (100 mL) and dried to give 5-amino-2,4,6-triiodoisophthalic acid (II) (64.61 g; 0.116 mol) as a whitish solid. Yield 83.8%. The product was analyzed by HPLC by comparison with a standard and fulfilled the analytical specifications for 5-amino-2,4,6-triiodoisophthalic acid industrially produced.

Example 6

In a 1 L jacketed reactor equipped with thermometer, condenser and mechanic stirrer, a solution of 5-aminoisophthalic acid (I) sodium salt in H$_2$O corresponding to 7.2% (w/w) of acid (277.7 g of solution; 0.110 mol) was loaded, diluted with H$_2$O (220 mL) and acidified with 96% H$_2$SO$_4$ (8.8 mL; 0.159 mol). Then ethanol (73 mL) and and I$_2$ (33.6 g; 0.132 mol) were added. The mixture was heated to 80-82° C. and a 32.6% (w/w) solution of HIO$_3$ in H$_2$O (35.62 g; 0.066 mol) was added dropwise in 3 h (mixture pH: 1.8). The mixture was kept to the above temperature for additional 4 h, then acidified at pH<1 with 50% H$_2$SO$_4$ (44 mL; 0.314 mol) and cooled down to 25° C. in 2 h. Sodium bisulfite (0.820 g; 4.31 mmol) was added under stirring, then the solid was filtered, washed with H$_2$O (100 mL) and dried to give 5-amino-2,4,6-triiodo-isophthalic acid (51.36 g; 0.092 mol) as pale pink solid. Yield 83%. The product was analyzed by HPLC by comparison with a standard and fulfilled the analytical specifications for 5-amino-2,4,6-triiodoisophthalic acid industrially produced.

Example 7

In a 1 L jacketed reactor equipped with thermometer, condenser and mechanic stirrer, a solution of 5-aminoisophthalic acid (I) sodium salt in H$_2$O corresponding to 6.7% (w/w) of acid (313.1 g of solution; 0.138 mol) was loaded, diluted with H$_2$O (200 mL) and acidified with 50% H$_2$SO$_4$ (41.15 g; 0.210 mol). Solid I$_2$ (42.03 g; 0.166 mol) was then added at room temperature and the obtained mixture was then heated at 75° C. A 0.66 M solution of HIO$_3$ in H$_2$O (140.0 g; 0.0833 mol) was added dropwise in 1 hour and the resulting mixture was kept under stirring at 75° C. for additional 4 hours. During all the heating ramp, the HIO$_3$ addition and the following completion time (4 hours) the pH of the reaction mixture was maintained at 3.0 by addition of 2M NaOH. The suspension was finally acidified at pH=1 with 50% H$_2$SO$_4$ (143 g; 0.729 mol), slowly added in 1.5 h, cooled to 25° C. in 2 hours. A 18% (w/w) solution of sodium bisulfite was added up to a redox potential of the suspension<than 250 mV. Then the solid was filtered, washed with H$_2$O (100 mL) and dried to give 5-amino-2,4,6-triiodoisophthalic acid (II) (66.0 g; 0.118 mol). Yield 85%. The product was analyzed by HPLC by comparison with a standard and fulfilled the analytical specifications for 5-amino-2,4,6-triiodoisophthalic acid industrially produced.

Comparative Example 1

This test was performed to evaluate the exploitability of the iodinating conditions disclosed in US 2007/0219396, suitably adapted in the iodinating agent amount, in order to provide a triiodinated derivative.

In a 25 mL three necked round bottom flask equipped with thermometer, condenser and magnetic stirrer, solid 5-aminoisophthalic acid (I) (1 g; 5.5 mmol), solid I$_2$ (1.61 g; 6.34 mmol) and acetic acid (15 mL) were added and stirred at 22° C. A 70% (w/w) solution of HIO$_3$ in H$_2$O (0.96 g; 3.8 mmol) was then added over 0.5 h.

Figure 3:
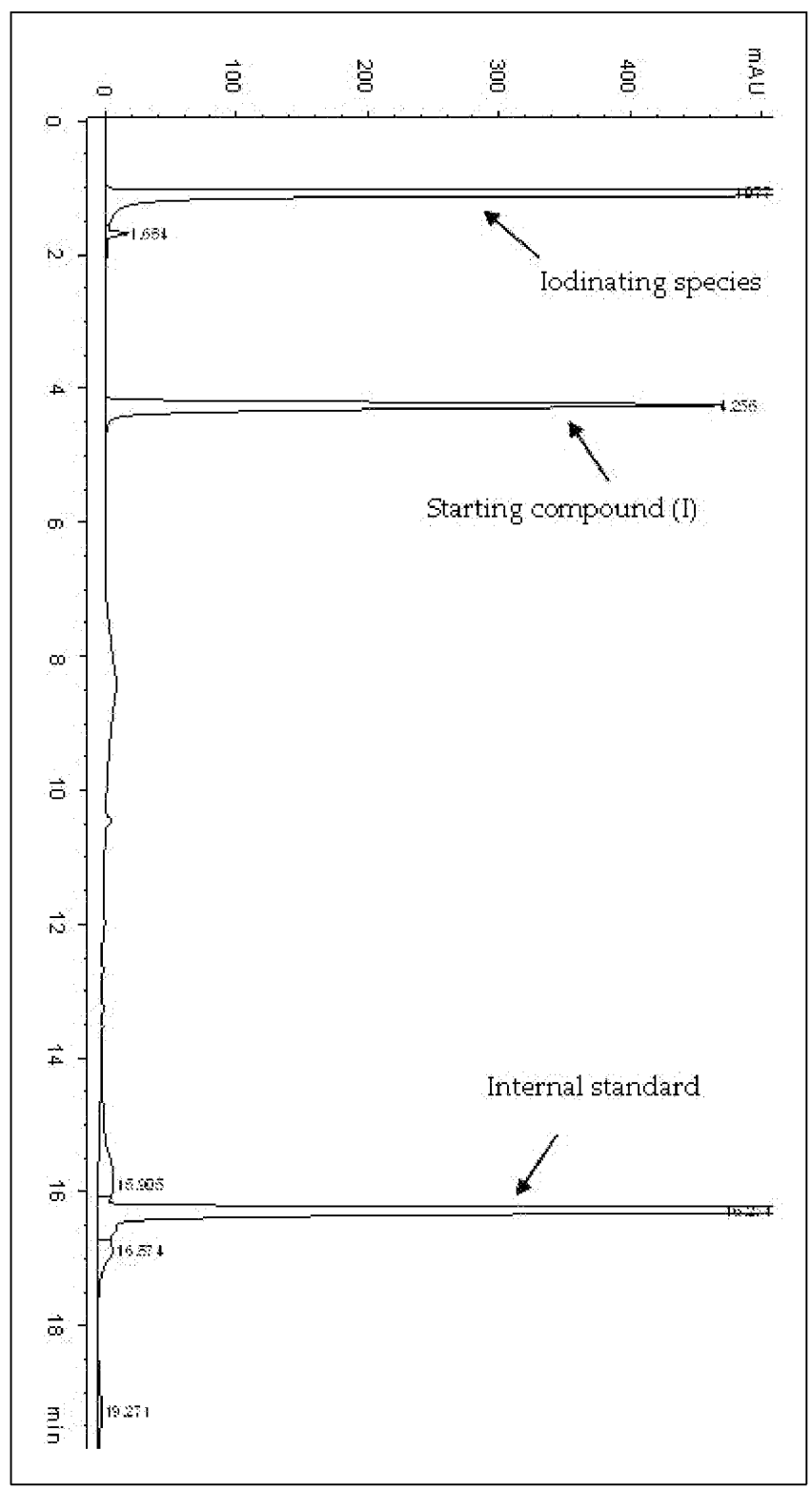
FIG. 3: HPLC analysis of the crude solution of Comparative Example 1, after 3 hours at 22° C.

In this respect, it is worth noting that due to the very low solubility of the iodic acid in acetic acid, the addition of the oxidizing agent at the concentration taught by the cited art, namely 70% w/w, leads to a non homogeneous mixture. The obtained mixture was kept at this temperature for 3 hours and then analysed by HPLC. Obtained chromatogram (FIG. 3) shows the total absence of any detectable conversion to a iodinated compound.

For purely exploratory purposes, not suggested by the cited application, the reaction mixture was then heated at 60° C. for additional 6 hours (total reaction time 9 h). The obtained dark mixture was then cooled at room temperature, without providing any crystallization or precipitation of the desired 5-amino-2,4,6-triiodoisophthalic acid (II).

Figure 4:
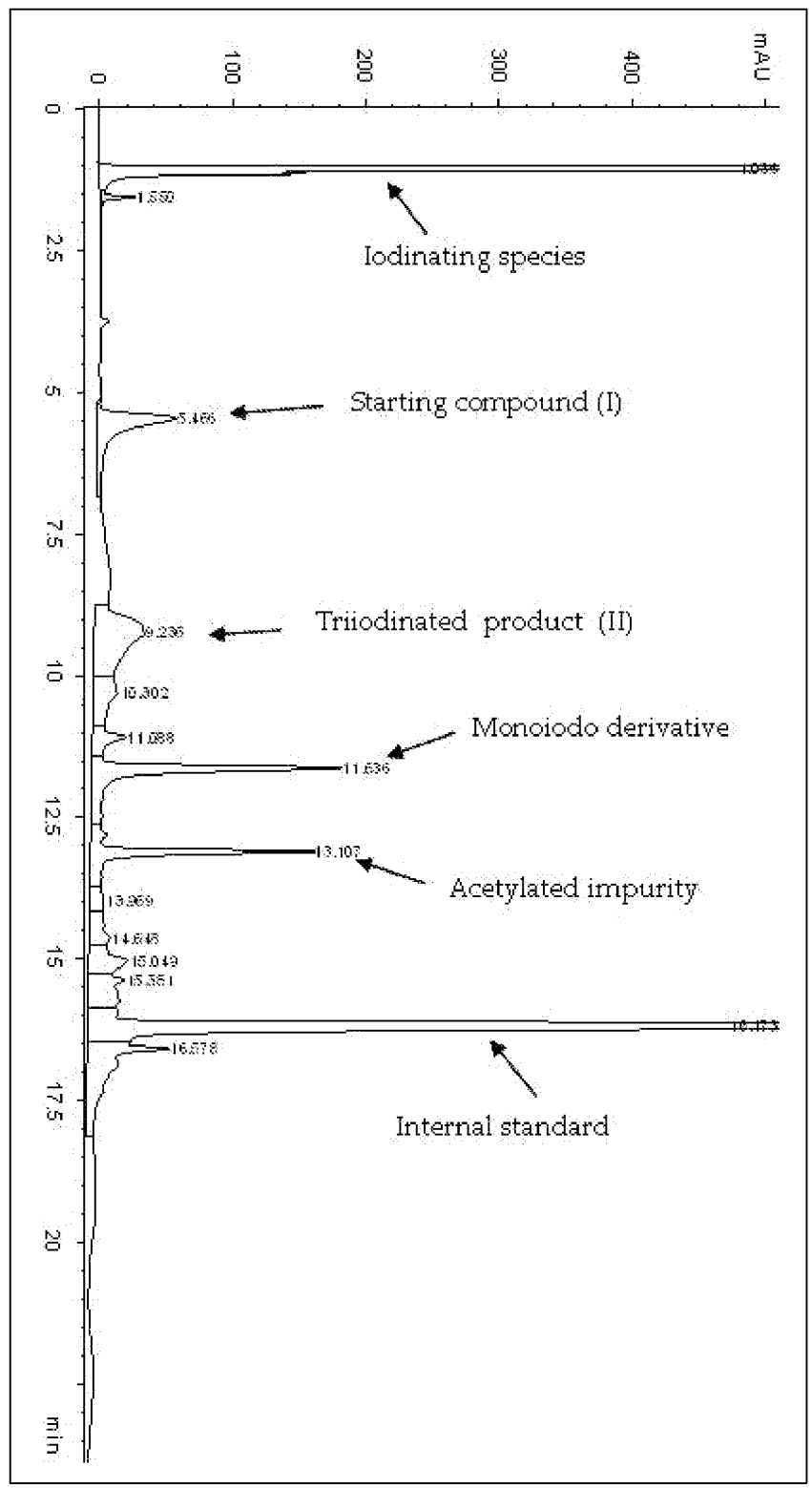
FIG. 4: HPLC analysis of the crude solution of Comparative Example 1, after 3 hours at 22° C. and additional 6 hours to 60° C.

The mixture was then analyzed by HPLC and the results, shown in FIG. 4, indicate the presence of a very little amount of triiodinated derivative, and, conversely, of a significant amount of an impurity identified as the N-acetil-5-aminoisophthalic acid of formula

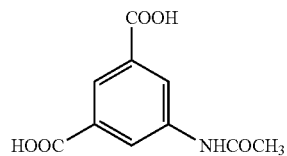

Comparative Example 2

This comparative example was performed to test the iodinating conditions disclosed by the former Chem. Ber. articles, especially by the *Chem. Ber.*, 1897 30 (2), 1943-1948 article, that provides some more experimental details allowing to try their reproduction.

Accordingly, we firstly tested the iodinating conditions taught by the cited art on the same substrate, namely 3-aminobenzoic acid, and by using the disclosed amount of iodinating agents, i.e. the stoichiometric amount requested for a hypothetical exhaustive diiodination of the substrate compound.

In this respect, however, it is worth noting that the molar ratio $I_2$:$HIO_3$ used and taught by the cited art, namely 2.8, is not appropriate for the complete transfer of the added iodine (considered as the sum of $I_2$ and $HIO_3$) to the aromatic substrate. In fact, and as formerly said, to have a complete transfer, the molar ratio between iodine and iodic acid must be 2 (theoretical ratio) or less.

Just to have a better idea of the used iodination conditions, the reaction pH has also been checked at different reaction times.

a. Iodination of 3-aminobenzoic Acid.

The iodinating solution was prepared by dissolution of $I_2$ (4 g; 15.74 mmol) in 20% aq. KOH (9.5 mL) to give a suspension of a white solid in a pale yellow solution, that turned into a clear solution when diluted with $H_2O$ (30 mL); then a solution of $HIO_3$ (1 g; 5.69 mmol) in $H_2O$ (10 mL) was added and the final dark solution was diluted to 250 mL with $H_2O$.

Figure 5:
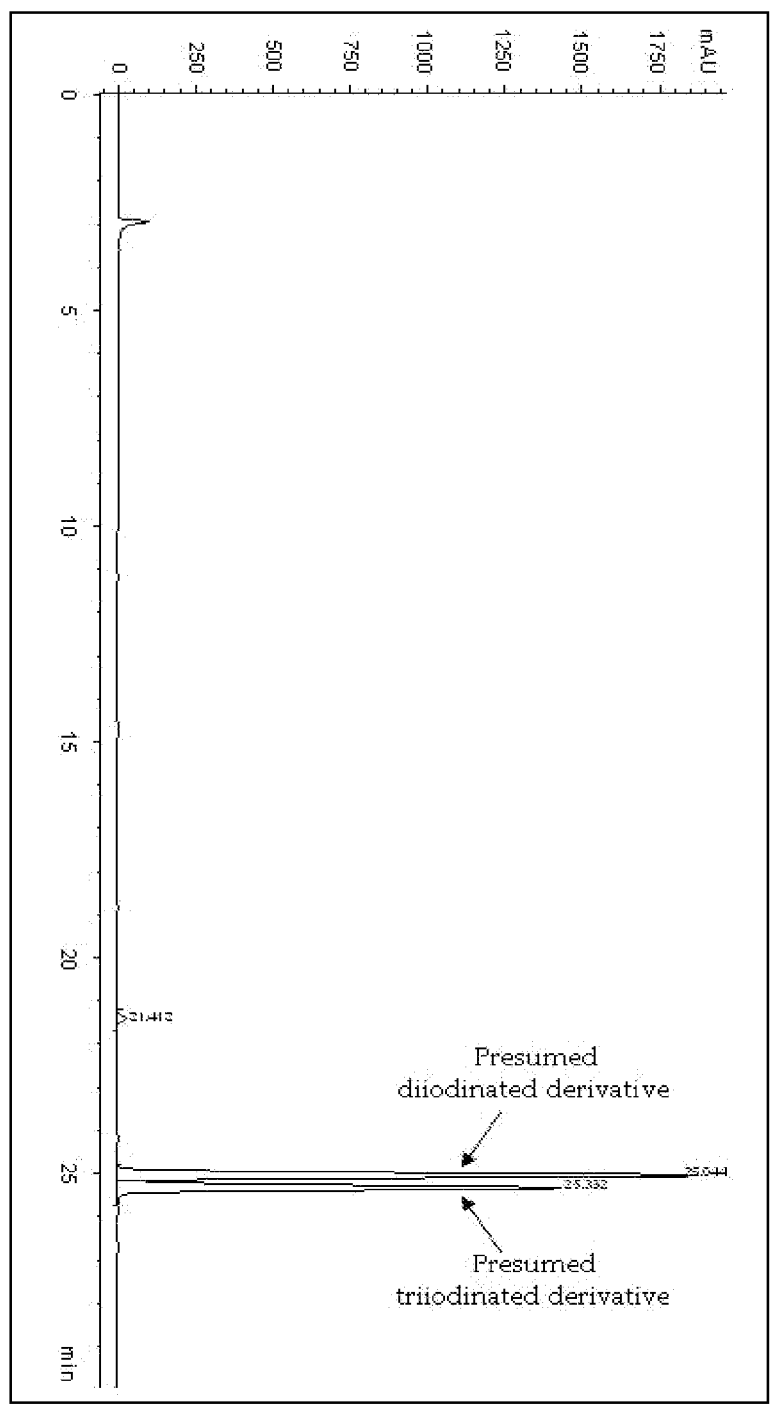
FIG. 5: HPLC analysis of the solid a1
Figure 6:
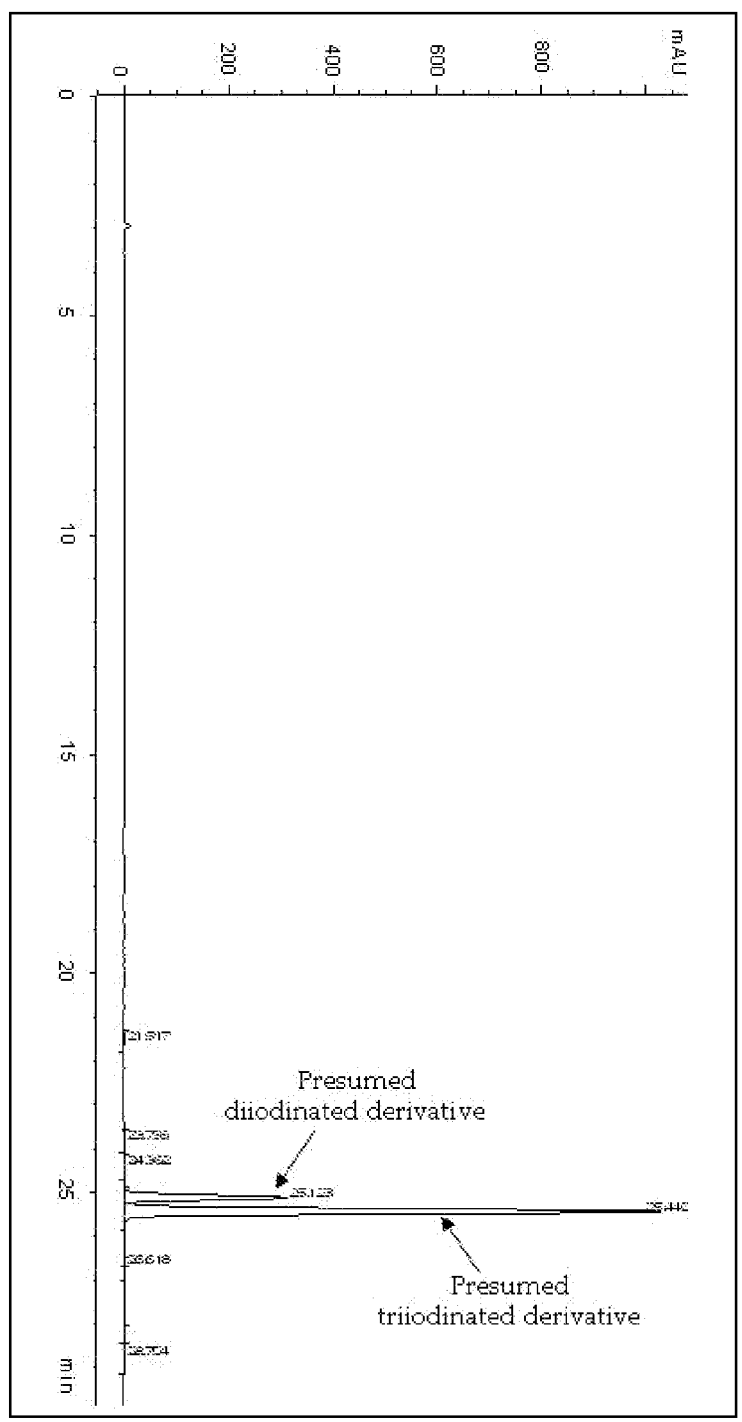
FIG. 6: HPLC analysis of the solid a2

The solution so obtained was added dropwise over 3 h to a acidic solution of 3-aminobenzoic acid (2.5 g; 18.23 mmol) in a mixture of $H_2O$ (500 mL) and 36-38% aq. HCl (50 mL) (solution pH: around 0) heated at 30° C. Once the addition was completed (pH 0.25), a solid started to crystallize. The reaction mixture was then stirred at room temperature for 12 h, then the solid was filtered, washed with $H_2O$ (15 mL), and dried to give a brownish solid a1 (2.3 g). In line with the description, additional iodinating solution, prepared as described above, (125 mL; $I_2$ 7.87 mmol; $HIO_3$ 2.85 mmol) was added drop wise over 2 h to the mother liquor kept at about 30° C., thus favoring the precipitation of another solid. After 12 h at room temperature this solid was filtered, washed with $H_2O$ and dried to give a brownish solid a2 (2.2 g). The HPLC analysis of the two solids obtained, (FIGS. 5 and 6, respectively), shows that both precipitates correspond to a mixture of two species contained, in the two cases, with different HPLC area % ratio, as reported in table 1 below.

TABLE 1

| Solid | HPLC (area %) | |
|---|---|---|
| | t.r. 25.1 min | t.r. 25.4 min |
| a1 | 54.3 | 44.9 |
| a2 | 22.1 | 76.4 |

By comparing the $^1$H-NMR spectra integrals of the two solids with the relative HPLC abundance of the two species, we could identify the component at t.r. 25.1 min as one of the three possible diiodo derivatives, and the component at t.r. 25.4 min as the triiodo derivative.

Figure 7:
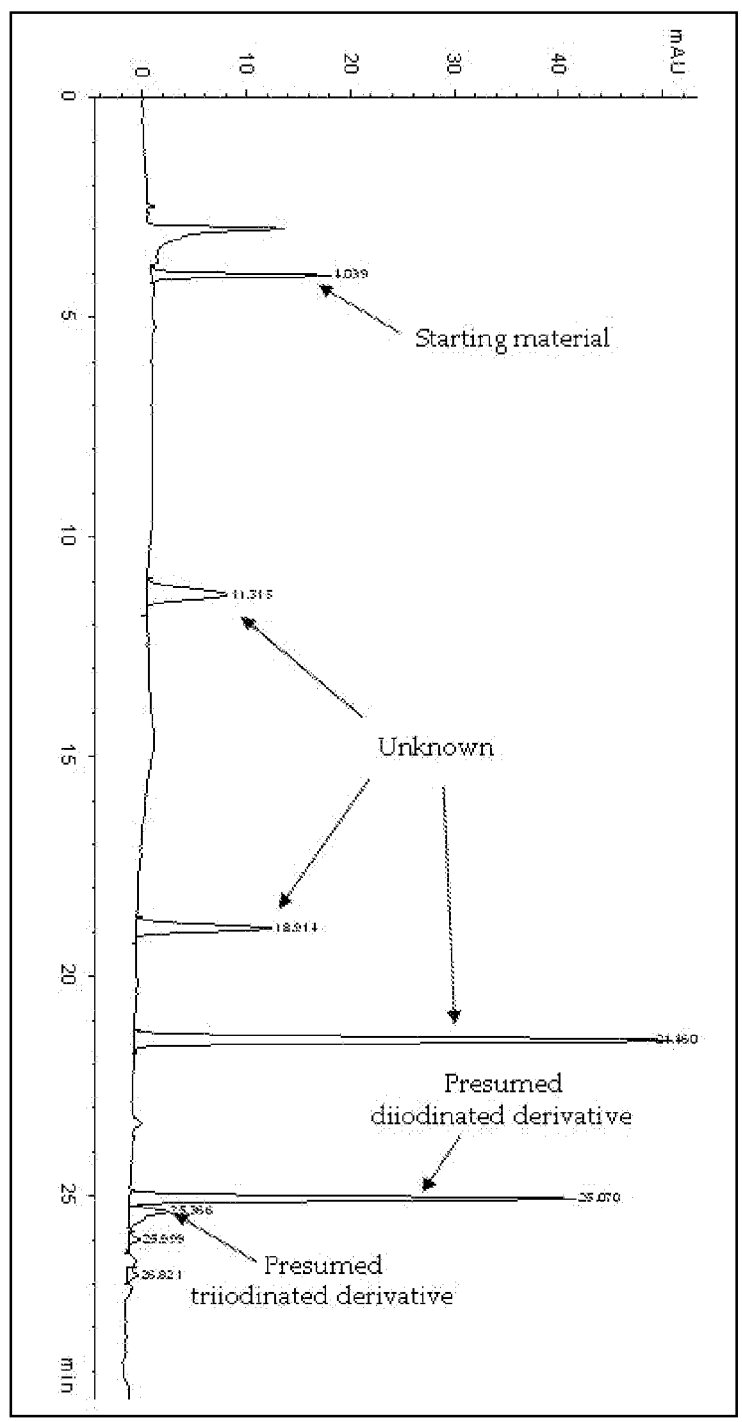
FIG. 7: HPLC analysis of the mother liquors of a2

On the other side, the HPLC analysis of the final mother liquor shows that unreacted 3-aminobenzoic substrate is still present in the liquor beside the component at t.r. 25.1 min and three unknown species, (FIG. 7) thus confirming that the iodination conversion was other than complete (the yield of obtained triiodo derivative could be roughly evaluated as around 30% of the theoretical), and the obtained product was other than pure.

b. Iodination of 5-aminoisophthalic Acid

These same iodinating conditions, properly adapted to may provide the desired triiodinated compound, were then tested on the substrate compound of the instant invention.

Figure 8:
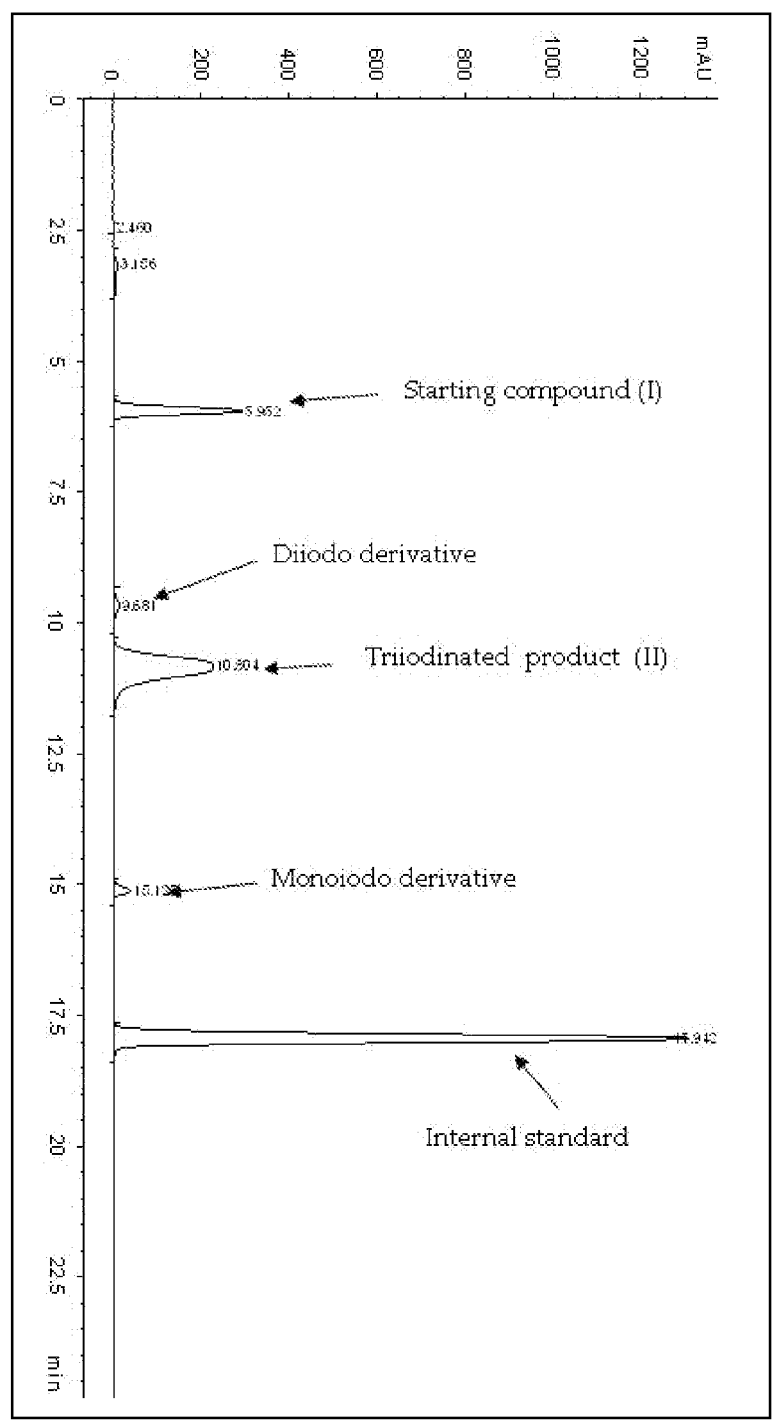
FIG. 8: HPLC analysis of the reaction mixture b1

Accordingly a iodinating solution was prepared as described above (114 mL, $I_2$ 7.18 mmol; $HIO_3$ 2.55 mmol,) and added dropwise to an acidic solution of 5-aminoisophthalic acid (I) (1 g; 5.52 mmol) in a mixture of $H_2O$ (150 mL) and 36-38% aq. HCl (15 mL) (pH around 0) heated at 30° C. In line with the prior art teaching, the mixture was then kept under stirring at 30° C. for 19 h without observing any crystallization or precipitation. The mixture (pH 0.33) was thus cooled down to room temperature and analyzed by HPLC. The observed results, reported in FIG. 8, confirm that the conversion of starting material was other than complete and a significant amount of the starting substrate is still present in the crude solution.

A quantization of the obtained 5-amino-2,4,6-triiodoisophthalic acid made versus an internal standard indicates a yield of 28.2%.

The invention claimed is:

1. A process for the preparation of 5-amino-2,4,6-triiodoisophthalic acid of formula (II)

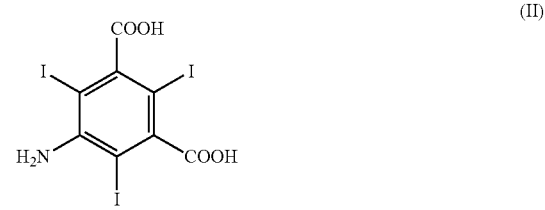 [SMILES: Nc1c(I)c(C(=O)O)c(I)c(C(=O)O)c1I]

(II)

comprising the iodination of 5-aminoisophthalic acid of formula (I)

(I)

or a salt thereof with molecular iodine and in the presence of iodic acid as an oxidizing agent, wherein the iodination reaction is carried out in a solvent selected from the group consisting of water, aqueous saline solution, hydroalcoholic mixture of lower alcohols $C_1$-$C_4$ and aqueous mixtures of dioxane or glycols, at a pH lower than 3.5.

2. The process according to claim 1 wherein the molar ratio between molecular iodine and 5-aminoisophthalic acid or a salt thereof is comprised from 1 to 1.3, and the molar ratio iodine to iodic acid is comprised from 1:0.5 to 1:0.8.

3. The process according to claim 2 in which the iodination of the 5-aminoisophthalic acid or a salt thereof with iodine and iodic acid is carried out by using a molar ratio of 5-aminoisophthalic acid or salt thereof: iodine:iodic acid of 1:1.2:0.6.

4. The process according to claim 1 carried out in the presence of an acid selected from phosphoric, methanesulfonic and sulfuric acid.

5. The process according to claim 1 wherein the solvent is water or an aqueous saline solution.

6. The process according to claim 1 that comprises adding molecular $I_2$ and iodic acid to an aqueous suspension of the 5-aminoisophthalic acid or salt thereof having a pH lower than 3.5.

7. The process according to claim 6 wherein the said aqueous suspension is obtained by direct acidification of a crude solution from an industrial process comprising 5-aminoisophthalic acid as sodium salt.

8. The process according to claim 6 wherein said pH is comprised from 1 to 3.

9. The process according to claim 1 carried out at a temperature comprised from 50° C. to 85° C.

10. The process according to claim 1 wherein the reaction time is comprised from 2 to 10 hours.

11. A process for the preparation of the compounds of formula (III)

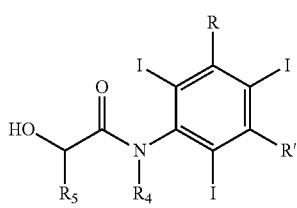

(III)

wherein:
R and R' represent, the same or different from each other, a group selected from carboxy (—COOH), carboxyester (—COOR$^1$) and carboxamido (—CONH$_2$, —CONHR$^1$ or —CONR$^2$R$^3$), wherein R$^2$ and R$^3$ are, the same or different from each other, a straight or branched C$_1$-C$_4$ alkyl group optionally substituted by one or more hydroxyl groups, and R$_4$ and R$_5$ are, the same or different from each other, hydrogen or a straight or branched C$_1$-C$_6$ alkyl group optionally substituted by one or more hydroxyl or C$_1$-C$_6$ alkoxy groups, said process comprising:
a) preparing an intermediate compound of formula (II) according to the process of claim 1; and
b) converting the compound of formula (II) to the compound of formula (III).

12. The process according to claim 11 for the preparation of a compound of formula (III) wherein both R and R' are a —CONH—CH(CH$_7$OH)$_2$ group, R$_4$ is hydrogen and R$_5$ is a methyl group.

13. The process according to claim 11 for the preparation of a compound of formula (III) in which both R and R' are a —CONH—CH$_2$—CH(OH)CH$_2$OH, R$_4$ is methyl and R$_5$ is hydrogen.

14. A process for the preparation of Iopamidol or Iomeprol characterized in that it comprises starting from a compound of formula (II) obtained according to the process of claim 1.

15. The process according to claim 12 comprising:
a) converting the compound of formula (II) into the corresponding acid dichloride,
b) condensing the Obtained dichloride with 2-[(acetyloxy)]propionic acid chloride, to give to the corresponding 5-carboxamido derivative, and
c) condensing the obtained intermediate with serinol and removing the acetyl protecting group to obtain the compound of formula (III).

* * * * *

UNITED STATES PATENT AND TRADEMARK OFFICE
CERTIFICATE OF CORRECTION

PATENT NO. : 9,238,615 B2
APPLICATION NO. : 13/265165
DATED : January 19, 2016
INVENTOR(S) : Attilio Citterio et al.

It is certified that error appears in the above-identified patent and that said Letters Patent is hereby corrected as shown below:

IN THE CLAIMS

Column 17, line 10, cancel the text beginning with "11. A process for the preparation of the compounds" to and ending with "to the compound of formula (III)." in column 18, line 9, and insert the following claim:

--11. A process for the preparation of the compounds of formula (III)

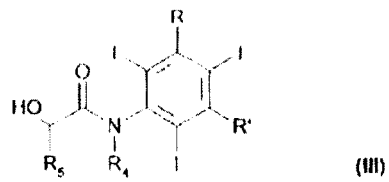

wherein:
R and R' represent, the same or different from each other, a group selected from carboxy (-COOH), carboxyester (-COOR$^1$) and carboxamido (-CONH$_2$, -CONHR$^1$ or –CONR$^2$R$^3$), wherein R$^1$, R$^2$ and R$^3$ are, the same or different from each other, a straight or branched C$_1$-C$_4$ alkyl group optionally substituted by one or more hydroxyl groups, and R$_4$ and R$_5$ are, the same or different from each other, hydrogen or a straight or branched C$_1$-C$_6$ alkyl group optionally substituted by one or more hydroxyl or C$_1$-C$_6$ alkoxy groups,
said process comprising:
    a) preparing an intermediate compound of formula (II) according to the process of claim 1; and
    b) converting the compound of formula (II) to the compound of formula (III).--

Signed and Sealed this
Twenty-first Day of June, 2016

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 9,238,615 B2 | Page 1 of 1 |
| APPLICATION NO. | : 13/265165 | |
| DATED | : January 19, 2016 | |
| INVENTOR(S) | : Attilio Citterio et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1100 days.

In the Claims:

Column 18, line 10, cancel the text beginning with "12. The process according to claim 11" to and ending with "is a methyl group." in column 18, line 13, insert the following claim:

--12. The process according to claim 14 for the preparation of a compound of formula (III) wherein both R and R' are a –CONH-CH(CH$_2$OH)$_2$ group, R$_4$ is hydrogen and R$_5$ is a methyl group.--

This certificate supersedes the Certificate of Correction issued June 21, 2016.

Signed and Sealed this
Ninth Day of August, 2016

Michelle K. Lee
*Director of the United States Patent and Trademark Office*